(12) United States Patent
Vu (10) Patent No.: US 12,270,878 B2
(45) Date of Patent: Apr. 8, 2025

(54) FMRI RECONSTRUCTION OF BRAIN-STATE-SPECIFIC IMAGES FROM SLOW, ANATOMICAL, MRI IMAGE DATA

(71) Applicant: UNITED STATES GOVERNMENT AS REPRESENTED BY THE DEPARTMENT OF VETERANS AFFAIRS, Washington, DC (US)

(72) Inventor: An Vu, Washington, DC (US)

(73) Assignee: UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 435 days.

(21) Appl. No.: 16/624,755

(22) PCT Filed: Jun. 28, 2018

(86) PCT No.: PCT/US2018/040134
§ 371 (c)(1),
(2) Date: Dec. 19, 2019

(87) PCT Pub. No.: WO2019/006199
PCT Pub. Date: Jan. 3, 2019

(65) Prior Publication Data
US 2021/0141040 A1 May 13, 2021

Related U.S. Application Data

(60) Provisional application No. 62/526,296, filed on Jun. 28, 2017.

(51) Int. Cl.
*G01R 33/54* (2006.01)
*A61B 5/00* (2006.01)
(Continued)

(52) U.S. Cl.
CPC ........ *G01R 33/4806* (2013.01); *A61B 5/0042* (2013.01); *A61B 5/055* (2013.01);
(Continued)

(58) Field of Classification Search
CPC ............ G01R 33/4806; G01R 33/4818; G01R 33/546; G01R 33/5611; G01R 33/567;
(Continued)

(56) References Cited

U.S. PATENT DOCUMENTS

| 2002/0103428 A1 | 8/2002 | deCharms |
| 2005/0154290 A1 | 7/2005 | Langleben |

(Continued)

OTHER PUBLICATIONS

Lin et al., K-space reconstruction of magnetic resonance inverse imaging (K-Inl) of human visuomotor systems, Neuroimage. Feb. 15, 2010; 49(4): 3086-3098 (Year: 2010).*

(Continued)

*Primary Examiner* — Joel Lamprecht
*Assistant Examiner* — Amy Shafqat
(74) *Attorney, Agent, or Firm* — Ballard Spahr LLP (57) ABSTRACT

Functional Magnetic Resonance Imaging (fMRI) reconstruction of brain-state-specific images from slow, anatomical MRI image data. In an embodiment, for each of a plurality of stimulation sequences, an fMRI apparatus is controlled to capture a set of whole-brain image data of the same region of a subject's brain according to the stimulation sequence. Each stimulation sequence is configured to induce each of a plurality of brain states in a different sequence than any of the other stimulation sequences, and each set of whole-brain image data comprises a plurality of sub-acquisition segments. For each set of whole-brain image data, each sub-acquisition segment in the set is associated with one of the brain states. Then, for each of the brain states, a whole-brain image is reconstructed from a subset of the (Continued)

sub-acquisition segments, in each captured set of whole-brain image data, that are associated with the brain state.

20 Claims, 5 Drawing Sheets

(51) Int. Cl.
    *A61B 5/055*     (2006.01)
    *G01R 33/48*     (2006.01)
    *G01R 33/561*     (2006.01)
    *G01R 33/567*     (2006.01)

(52) U.S. Cl.
    CPC ....... *G01R 33/4818* (2013.01); *G01R 33/546* (2013.01); *G01R 33/5611* (2013.01); *G01R 33/567* (2013.01)

(58) Field of Classification Search
    CPC ....... A61B 5/0042; A61B 5/055; A61B 5/145; A61B 5/1477; A61B 5/16
    See application file for complete search history.

(56) References Cited

U.S. PATENT DOCUMENTS

| | | |
|---|---|---|
| 2014/0180060 A1 | 6/2014 | Parrish et al. |
| 2015/0297444 A1 | 10/2015 | Tass |
| 2015/0366482 A1 | 12/2015 | Lee |
| 2017/0021161 A1* | 1/2017 | De Ridder ......... A61N 1/36067 |
| 2017/0128025 A1* | 5/2017 | Chen ................... G01R 33/5673 |
| 2019/0251450 A1* | 8/2019 | McIntosh ................ G06N 3/10 |

OTHER PUBLICATIONS

Siemens Medical, MAGNETOM Trio a Tim System Operator Manual—MR System, available online on Mar. 13, 2011. (Year: 2011).*

* cited by examiner

FMRI RECONSTRUCTION OF BRAIN-STATE-SPECIFIC IMAGES FROM SLOW, ANATOMICAL, MRI IMAGE DATA

CROSS-REFERENCE TO RELATED APPLICATIONS

This application is a national stage filing under 35 U.S.C. § 371 of International Application No. PCT/US2018/040134, filed on Jun. 28, 2018, which claims priority to U.S. Provisional Patent App. 62/526,296, filed on Jun. 28, 2017, the entirety of which are hereby incorporated herein by reference.

BACKGROUND

Field of the Invention

The present invention generally relates to functional Magnetic Resonance Imaging (fMRI) and, more particularly, to generating one or more whole-brain fMRI images that each correspond to a single brain state of a subject.

Related Art

The most common conventional method for non-invasively studying human brain function is a form of fMRI. This particular technique is chosen because it is fast enough to image the entire brain every few seconds at a spatial resolution of up to approximately 0.5 mm$^3$ resolution. However, this resolution is generally insufficient to study more detailed brain functional organization, known to exist from animal and post-mortem human anatomical studies. Thus, while traditional fMRI is able to acquire images quickly, the resulting images are not of a sufficient resolution for studying detailed brain functional organization.

The study of detailed, mesoscale brain functional organization generally requires a spatial resolution of 0.03 mm$^3$ or greater. Anatomical MRI can image at this higher spatial resolution, but unfortunately, takes on the order of ten minutes to scan the entire brain. This is much too slow to capture fluctuations in brain signals, which may occur on the order of seconds. Thus, anatomical MRI images, while providing sufficient resolution to study detailed brain functional organization, will represent blurring between the different brain states that came and went during the time required to acquire the images.

Therefore, what is needed is a system and method that overcomes these significant problems found in conventional systems. For instance, it would be advantageous to be able to acquire anatomical MRI images, with spatial resolution of 0.03 mm$^3$ or greater, but without blurring between different brain states.

SUMMARY

Accordingly, in an embodiment, a method is disclosed which comprises using at least one hardware processor to: for each of a plurality of stimulation sequences, control a functional Magnetic Resonance Imaging (fMRI) apparatus to capture a set of whole-brain image data of the same region of a brain of a subject according to the stimulation sequence, wherein each of the plurality of stimulation sequences is configured to induce each of a plurality of brain states in a different sequence than any of the other plurality of stimulation sequences, and wherein each set of whole-brain image data comprises a plurality of sub-acquisition segments; for each captured set of whole-brain image data, associate each of the plurality of sub-acquisition segments in the set of whole-brain image data with one of the plurality of brain states; and, for each of the plurality of brain states, reconstruct a whole-brain image from a subset of the plurality of sub-acquisition segments, in each captured set of whole-brain image data, that are associated with the brain state. This method may be embodied in executable software modules of a processor-based system and/or in executable instructions stored in a non-transitory computer-readable medium.

Other features and advantages of the present invention will become more readily apparent to those of ordinary skill in the art after reviewing the following detailed description and accompanying drawings.

BRIEF DESCRIPTION OF THE DRAWINGS

The structure and operation of the disclosed embodiments will be understood from a review of the following detailed description and the accompanying drawings in which like reference numerals refer to like parts and in which.

DETAILED DESCRIPTION

The disclosed embodiments generate one or more whole-brain fMRI images, which each correspond to a single brain state of a subject, from a plurality of raw whole-brain fMRI image data that each represent a plurality of brain states of the subject. For example, an embodiment disclosed herein captures a plurality of sets of whole-brain fMRI image data of a subject's brain, where each set of whole-brain fMRI image reflects two or more different brain states. This raw fMRI image data may be granularly labeled or otherwise associated with the coincident brain state (e.g., by correlating a time at which the image data was captured with a time at which the subject was stimulated by a particular stimulus configured to induce the coincident brain state), such that all of the raw fMRI image data, corresponding to a particular brain state, may be reconstructed into a single whole-brain fMRI image of that particular brain state.

As used herein, the terms "image" and "image data" encompass any non-raw, image-space fMRI data and raw k-space (i.e., the spatial frequency domain) fMRI data, respectively, that represents an image or portion of an image of the subject's brain. As is well-known in the art, a representation of fMRI data in k-space can be converted into image-space using a Fourier transform, and the representation of fMRI data in image-space can be converted into k-space using the inverse Fourier transform. The embodiments disclosed herein can be applied to image data in both k-space and image-space. However, the physical constraints to achieve higher isotopic resolutions are such that it is generally more efficient to apply the disclosed embodiments to image data in k-space (e.g., as opposed to slices in image-space), after which the reconstructed image data can be converted from k-space into image-space (e.g., for purposes of human visualization or other applications).

In addition, as used herein, the terms "whole-brain fMRI image" and "whole-brain fMRI image data" do not necessarily mean a representation of the entire brain of the subject in all three dimensions. Rather, the terms "whole-brain fMRI image" and "whole brain fMRI image data" encompass one or more representations of the entire brain in two dimensions at a certain depth (e.g., a representation of a slice of the subject's brain, at a horizontal or vertical depth, in k-space or image-space). However, it should be understood that the terms "whole-brain fMRI image" and "whole brain fMRI image data" also encompass a representation of the entire brain of the subject in all three dimensions (e.g., a plurality of representations of different slices of the subject's brain, at varying vertical and/or horizontal depths, in k-space or image-space). In other words, the term "whole-brain," as used herein, encompasses a single cross-section of the brain, as well as any plurality of cross-sections of the brain (i.e., at least a portion of the brain in three dimensions), including all cross-sections of the brain (i.e., the entire brain in three dimensions).

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

1. System Overview

Figure 1:
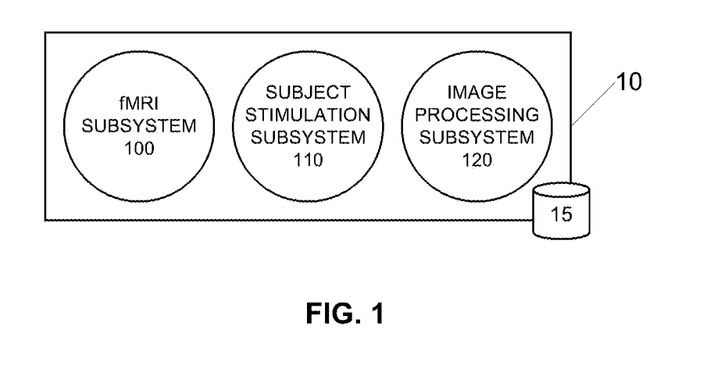
FIG. 1 is a block diagram illustrating an example system for acquiring fMRI images, according to an embodiment.

FIG. 1 is a block diagram illustrating an example system 10 for acquiring fMRI images, according to an embodiment. In the illustrated embodiment, system 10 comprises an fMRI subsystem 100, a subject-stimulation subsystem 110, and an image-processing subsystem 120. The illustrated subsystems may be integrated into a single apparatus or may be distributed among a plurality of devices that are communicatively coupled with each other, for example, by a computer network. System 10 and/or each of its individual components may be implemented on a processing device having a data storage area 15. An example processing device is described later with respect to FIG. 5.

fMRI subsystem 100 is configured to acquire fMRI image data from a subject positioned in fMRI subsystem 100, and generate fMRI images of the subject based on the acquired image data. fMRI subsystem 100 may also store acquired image data and fMRI images in data storage area 15.

Subject-stimulation subsystem 110 is configured to provide instructions and/or sensory stimulation to a subject positioned in fMRI subsystem 100. Subject-stimulation subsystem 110 may include any combination of a visual display monitor, an audio speaker, a user input device (e.g., keyboard, keypad, touch sensor, other hardware or software buttons, eye-tracking input device, microphone, etc.), a tactile stimulator (e.g., haptic motor), an olfactory stimulator, and/or the like. The function of subject-stimulation system 110 is to modulate brain activity in the subject. For example, subject-stimulation system 110 may control the visual display monitor to provide visual stimuli (e.g., text, images, video, animations, colors, instructions and/or outputs for the subject to perform mental tasks, etc.) to a subject, control the audio speaker to provide auditory stimuli (e.g., sounds, voice instructions for the subject to perform mental tasks, etc.) to the subject, control the user input device to receive inputs (e.g., a user's answer to a mental task, other input representing the completion of a mental task, etc.) from the subject, control the tactile stimulator to vibrate or provide some other tactile stimulation to the subject, and/or control the olfactory stimulator to release an odor or aroma within fMRI subsystem 100 (e.g., within a chamber of fMRI subsystem 100 within a vicinity of the subject's nostrils).

Subject-stimulation system 110 is configured to operate cooperatively with fMRI subsystem 100 to synchronize stimulation of the subject by subject-stimulation system 110 with the acquisition of fMRI image data by fMRI subsystem 100. For example, subject-stimulation system 110 may timestamp fMRI image data, timestamp each stimulus provided to the subject, and correlate those timestamps to associate the timestamps associated with the fMRI image data to the timestamps associated with any stimuli, to correlate any fMRI image data, which represents brain activity resulting from a particular stimulus, to that particular stimulus.

Image-processing subsystem 120 is configured to process fMRI image data, acquired by fMRI subsystem 100 and generally representing multiple brain states of a subject, and generate one or more whole-brain fMRI images that each corresponds to only a single brain state of the subject. For example, image-processing subsystem 120 may be configured to access acquired fMRI image data, stored in data storage area 15 by fMRI subsystem 100, and selectively combine portions of the acquired fMRI image data according to a brain state of the subject. Advantageously, this reconstruction of selected portions of the acquired fMRI image data, according to a brain state of the subject, into an fMRI image may be carried out by image-processing subsystem 120 or by fMRI subsystem 100. The resulting fMRI image may be stored in data storage area 15 and/or provided to a recipient via a computer network or a portable data storage device.

2. Process Overview

Figure 2A:
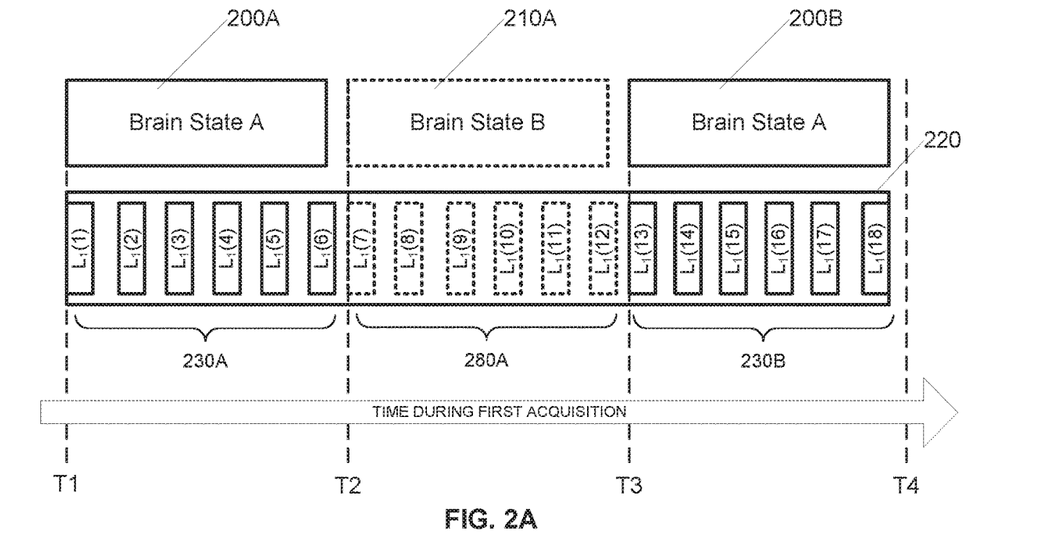
FIG. 2A is a block diagram illustrating an example of fMRI image data, acquired according to an embodiment.
Figure 2B:
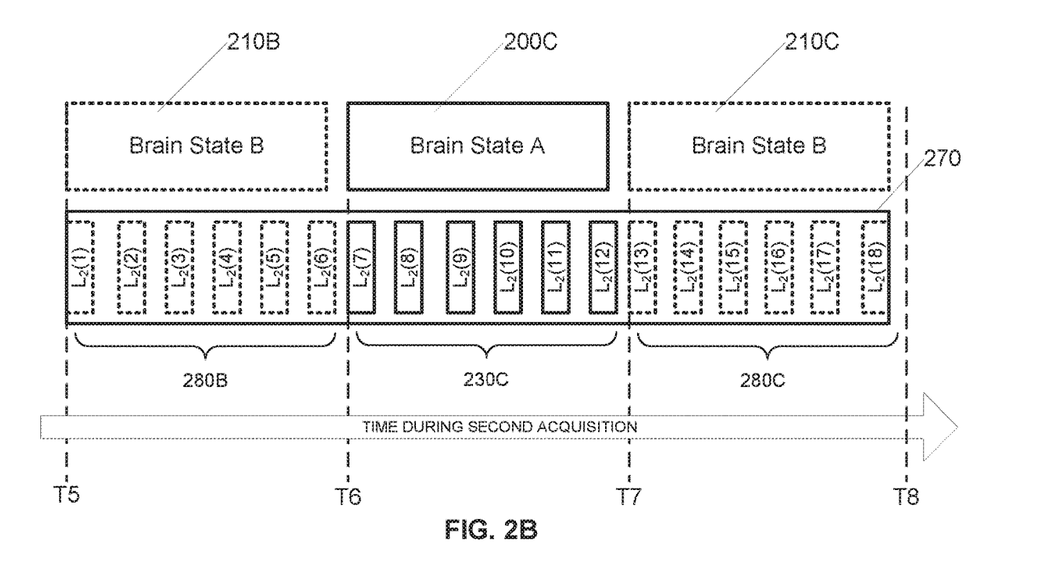
FIG. 2B is a block diagram illustrating an example of fMRI image data, acquired according to an embodiment.

FIGS. 2A and 2B illustrate two acquisitions of the same region of a subject's brain, according to an embodiment. Due to the length of time required for fMRI subsystem 100 to acquire fMRI image data, a particular brain state may only be active for a fraction of the time necessary to capture a whole-brain image. For example, as illustrated in FIG. 2A, fMRI subsystem 100 requires a time period from T1 to T4 (e.g., typically on the order of tens or hundreds of seconds) to acquire a whole-brain image. However, Brain State A is only active for a fraction of this time period, from T1 to T2, and then is inactive, while Brain State B is active, from at least T2 to T3. Thus, the whole-brain fMRI image that is captured from time T1 to T4 will comprise blurring between the different brain states (i.e., Brain States A and B, in the illustrated example), since one portion (i.e., sub-acquisition segment L) of the image data will have been captured while one brain state was active (e.g., Brain State A), while another portion of the image data will have been captured while a different brain state was active (e.g., Brain State B). The disclosed embodiments essentially remove this blurring by capturing N sets of whole-brain fMRI image data of the subject's brain in different sequences of N brain states, such that, overall, each sub-acquisition segment L of the subject's brain is captured across all N sets of whole-brain fMRI image data in all N brain states, and then re-sorting these sub-acquisition segments L according to each of the N brain states to produce N reconstructed whole-brain fMRI images (e.g., one or more two-dimensional slices or the entire three-dimensional images of the brain), which each correspond to one of the N brain states.

As mentioned above, FIG. 2A is a block diagram illustrating an example acquisition of fMRI image data 220 for at least a region of the subject's brain, according to an embodiment. In the illustrated embodiment, during the time period T1 to T4 in which fMRI image data 220 is being acquired, the subject transitions through a plurality of brain states: Brain State A 200A from T1 to T2; Brain State B 210A from T2 to T3; and Brain State A 200B from T3 to T4. As will be understood by the skilled artisan, in a more complicated real-world example, there may be many more than the two different brain states shown in the illustrated embodiment. fMRI subsystem 100 acquires fMRI image data 220 in a plurality of sub-acquisition segments $L_1(1)$ through $L_1(18)$ that collectively form whole-brain fMRI image data 220 (e.g., which represents one two-dimensional slice of the subject's brain, or one k-space line of the subject's brain). In a real-world example, acquired fMRI image data 220 may comprise many more sub-acquisition segments than the eighteen shown. Furthermore, the temporal resolution (e.g., from T1 to T2) of this technique can be as fine as the duration of a single sub-acquisition segment, which is typically on the order of seconds. In other words, one or more of the brain states may only be active for a single sub-acquisition segment L, instead of for the six sub-acquisition segments illustrated in FIGS. 2A and 2B.

In an embodiment, system 10 (e.g., fMRI subsystem 100 or image-processing subsystem 120) associates each sub-acquisition segment $L_1$ of fMRI image data 220 with a timestamp that indicates when that sub-acquisition segment was acquired. For example, sub-acquisition segment $L_1(1)$ may be associated with timestamp T1, sub-acquisition segment $L_1(2)$ may be associated with timestamp $T1+\Delta t_1$ (wherein $\Delta t_1$ represents the time needed to acquire sub-acquisition segment $L_1(1)$), sub-acquisition segment $L_1(3)$ may be associated with timestamp $T1+\Delta t_1+\Delta t_2$ (wherein $\Delta t_2$ represents the time needed to acquire sub-acquisition segment $L_1(2)$), and so on and so forth. In addition, system 10 (e.g., fMRI subsystem 100 or image-processing subsystem 120) may associate each sub-acquisition segment $L_1$ of fMRI image data 220 with a location corresponding to a region of the brain and/or line in k-space represented by that sub-acquisition segment.

In an embodiment, system 10 (e.g., subject-stimulation subsystem 110) may record a timestamp indicating the time at which each stimulus was applied to the subject in association with the applied stimulus. For instance, timestamps T1 and T3 may be recorded in association with an indication that a stimulus, designed to induce Brain State A in the subject, was applied to the subject. In addition, timestamp T2 may be recorded in association with an indication that a stimulus, designed to induce Brain State B in the subject, was applied to the subject. However, it should be understood that, in the event that Brain State B is simply the absence of Brain State A, the "stimulus" designed to induce Brain State B may simply be the termination of the stimulus designed to induce Brain State A. In this case, Brain State A represents an "on" or "stimulated" state, whereas Brain State B represents an "off" or "unstimulated" state.

Advantageously, since the time at which each individual sub-acquisition segment $L_1$ is known and the time at which each brain-state-inducing stimulus was provided is known, each timestamped individual sub-acquisition segment $L_1$ can be associated with a brain state (e.g., Brain State A 200 or Brain State B 210) that was active at the time that the individual sub-acquisition segment was captured. For example, as illustrated in FIG. 2A, the timestamped individual sub-acquisition segments 230A (i.e., $L_1(1)$-$L_1(6)$) are associated with brain state 200A, the timestamped individual sub-acquisition segments 280A (i.e., $L_1(7)$-$L_1(12)$) are associated with brain state 210A, and the timestamped individual sub-acquisition segments 230B (i.e., $L_1(13)$-$L_1(18)$) are associated with brain state 200B. Notably, brain states 200A and 200B both correspond to the same Brain State A, while brain state 210A corresponds to a different Brain State B.

FIG. 2B is a block diagram illustrating an example acquisition of fMRI image data 270, according to an embodiment. fMRI image data 270 represents the same region of the subject brain's as fMRI image data 220. However, fMRI image data 270 is acquired while activating the same brain states as were activated during the acquisition of fMRI image data 220, but in an inverse sequence. Specifically, in the illustrated embodiment, during the time period T5 to T8 in which fMRI image data 270 is being acquired, the subject transitions through the same plurality of brain states in inverse order: Brain State B 210B from T5 to T6 (as the inverse of Brain State A 200A from T1 to T2); Brain State A 200C from T6 to T7 (as the inverse of Brain State B 210A from T2 to T3); and Brain State B 210C from T7 to T8 (as the inverse of Brain State A 200B from T3 to T4). As with the first acquisition of fMRI image data 220, fMRI subsystem 100 acquires fMRI image data 270 in a plurality of sub-acquisition segments $L_2(1)$ through $L_2(18)$ that collectively form whole-brain fMRI image data 270. Each sub-acquisition segment $L_2$ represents the same portion of the subject's brain as a corresponding one of sub-acquisition segments $L_1$ (e.g., because they were acquired at the same timing from the start of the respective acquisitions). For example, $L_2(1)$ represents the same portion of the subject's brain as $L_1(1)$, but while a different brain state was active (i.e., Brain State B 210B for $L_2(1)$, and Brain State A 200A for $L_1(1)$). Similarly, $L_2(2)$ corresponds to $L_1(2)$, $L_2(7)$ corresponds to $L_1(7)$, $L_2(13)$ corresponds to $L_1(13)$, and so on and so forth.

As with fMRI image data 220, system 10 (e.g., fMRI subsystem 100 or image-processing subsystem 120) associates each sub-acquisition segment $L_2$ of fMRI image data 270 with a timestamp that indicates when that sub-acquisition segment was acquired. For example, sub-acquisition segment $L_2(1)$ may be associated with timestamp T5, sub-acquisition segment $L_2(2)$ may be associated with timestamp $T5+\Delta t_1$ (wherein $\Delta t_1$ represents the time needed to acquire sub-acquisition segment $L_2(1)$), sub-acquisition segment $L_2(3)$ may be associated with timestamp $T1+\Delta t_1+\Delta t_2$ (wherein $\Delta t_2$ represents the time needed to acquire sub-acquisition segment $L_2(2)$), and so on and so forth. In addition, system 10 (e.g., fMRI subsystem 100 or image-processing subsystem 120) may associate each sub-acquisition segment $L_2$ of fMRI image data 270 with a location corresponding to a region of the brain and/or line in k-space represented by that sub-acquisition segment.

In addition, as with fMRI image data 220, system 10 (e.g., subject-stimulation subsystem 110) may record a timestamp indicating the time at which each stimulus was applied to the subject in association with the applied stimulus. For instance, timestamp T6 may be recorded in association with an indication that a stimulus, designed to induce Brain State A in the subject, was applied to the subject. In addition, timestamps T5 and T7 may be recorded in association with an indication that a stimulus, designed to induce Brain State B in the subject, was applied to the subject, and/or an indication that the stimulus, designed to induce Brain State A in the subject, was not applied to the subject, thereby implying that Brain State B was active.

Again, since the time at which each individual sub-acquisition segment $L_2$ is known and the time at which each brain-state-inducing stimulus was provided is known, each timestamped individual sub-acquisition segment $L_2$ can be associated with a brain state (e.g., Brain State A 200 or Brain State B 210) that was active at the time that the individual sub-acquisition segment was captured. For example, as illustrated in FIG. 2B, the timestamped individual sub-acquisition segments 280B (i.e., $L_2(1)$-$L_2(6)$) are associated with brain state 210B, the timestamped individual sub-acquisition segments 230C (i.e., $L_2(7)$-$L_2(12)$) are associated with brain state 200C, and the timestamped individual sub-acquisition segments 280C (i.e., $L_2(13)$-$L_2(18)$) are associated with brain state 210C. Notably, brain state 200C corresponds to the same Brain State A as brain states 200A and 200B in FIG. 2A, while brain states 210B and 210C both correspond to the same Brain State B as brain state 210A in FIG. 2A.

To summarize, in the first acquisition, illustrated in FIG. 2A, a first set of whole-brain fMRI image data 220 of a region of the subject's brain (e.g., a two-dimensional slice of the subject's brain or the entire subject's brain in three dimensions) is captured from time T1 to T4, while at least two different brain states are activated (e.g., triggered) in a first sequence (i.e., A-B-A). In the second acquisition, illustrated in FIG. 2B, a second set of whole-brain fMRI image data of the same region of the subject's brain (e.g., the same slice of the subject's brain or the entire subject's brain in three dimensions) is captured from time T5 to T8, while the same brain states are triggered, but in a second sequence that is inverse to the first sequence (i.e., B-A-B). Thus, each sub-acquisition segment L has been captured in each of the two brain states A and B. Specifically, L(1)-L(6) were each captured in Brain State A by the first acquisition and Brain State B by the second acquisition, L(7)-L(12) were each captured in Brain State B by the first acquisition and Brain State A by the second acquisition, and L(13)-L(18) were each captured in Brain State A by the first acquisition and Brain State B by the second acquisition.

This technique can be extrapolated for any number of N brain states. For example, in the case of three brain states, A, B, and C, where each brain state is activated for roughly one-third of the acquisition time, there would be three acquisitions, instead of two. In a first acquisition, the brain states may be triggered in the sequence A-B-C. In the second acquisition, the brain states may be triggered in the sequence C-A-B. In the third acquisition, the brain states may be triggered in the sequence B-C-A. Alternatively, if each brain state is activated for roughly one-sixth of the acquisition time, the triggered sequences may be A-B-C-A-B-C in the first acquisition, C-A-B-C-A-B in the second acquisition, and B-C-A-B-C-A in the third acquisition. As another alternative, if each brain state is activated for roughly one-fourth of the acquisition time, the triggered sequences may be A-B-C-A in the first acquisition, B-C-A-B in the second acquisition, and C-A-B-C in the third acquisition. In any case, after three acquisitions, each sub-acquisition segment L has been captured in each of the three brain states A, B, and C. Larger sets of brain states (e.g., four, five, ten, one hundred, etc.) may be captured in a similar manner. In general, it will take N acquisitions to acquire each of the sub-acquisition segments L in each of N brain states. It should be understood that a set of N stimulation sequences can be determined for any N brain states, active for any fraction of the time required to capture the whole-brain fMRI image data. In addition, each stimulation sequence can induce the N brain states to fill the entire time required to capture the whole-brain fMRI image data.

Figure 2C:
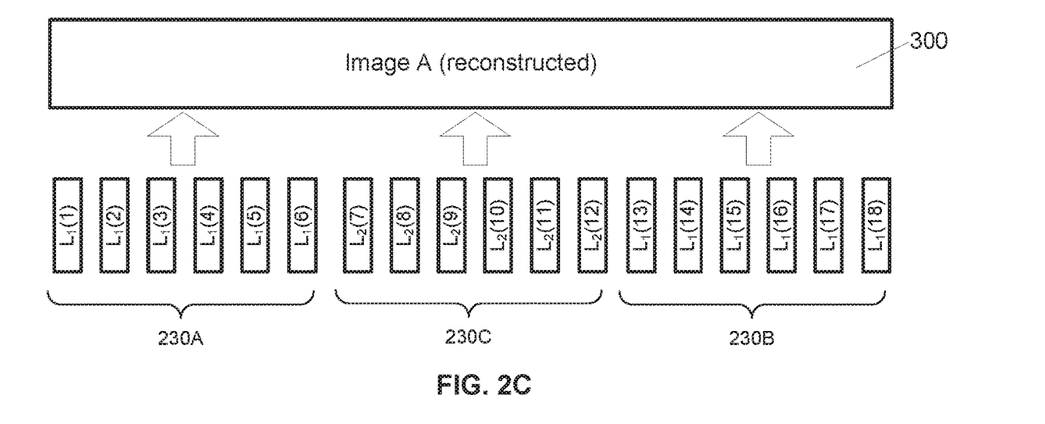
FIG. 2C is a block diagram illustrating an example reconstructed whole-brain fMRI image of a first brain state, according to an embodiment.
Figure 2D:
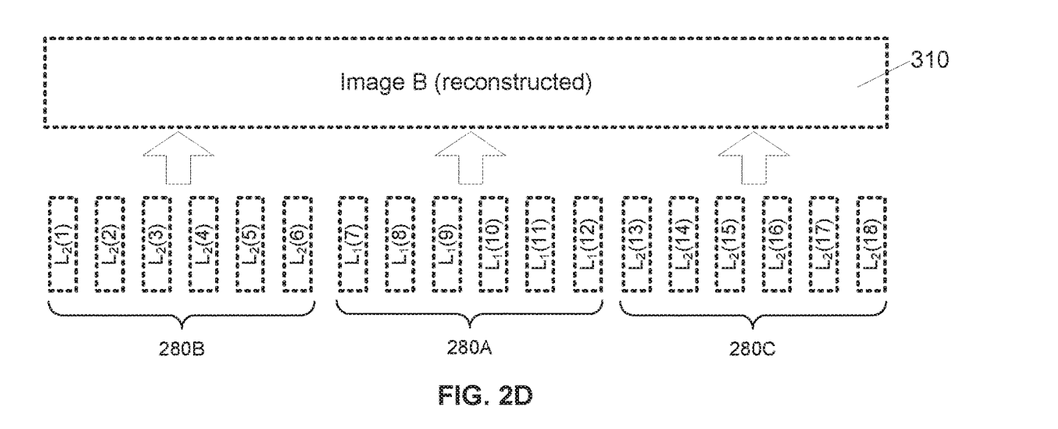
FIG. 2D is a block diagram illustrating an example reconstructed whole-brain fMRI image of a second brain state, according to an embodiment.

FIGS. 2C and 2D illustrate an example reconstruction of two whole-brain fMRI images 300 and 310, from the sub-acquisition segments L of fMRI image data 220 and 270, according to an embodiment. Each whole-brain fMRI image 300 and 310 represents a single brain state, and fMRI image 300 represents a different brain state than fMRI image 310. Specifically, fMRI image 300 represents only Brain State A, whereas fMRI image 310 represents only Brain State B. In other words, every portion of whole-brain fMRI image 300 represents the subject's brain while only Brain State A is active, and every portion of whole-brain fMRI image 310 represents the subject's brain while only Brain State B is active. In essence, system 10 (e.g., image-processing subsystem 120) deconstructs each of whole-brain fMRI image data 220 and 270, which each represents a plurality of blurred brain states, into sub-acquisition segments, and then reconstructs the deconstructed sub-acquisition segments into whole-brain fMRI images 300 and 310, which each represent only a single, exclusive, non-blurred brain state.

In an embodiment, system 10 (e.g., fMRI subsystem 100) stores each sub-acquisition segment L, captured during each acquisition, in association with its corresponding brain state (e.g., via direct association, indirect association via matching timestamps, etc.) in data storage area 15. As acquisitions are completed for a given whole-brain region of the subject's brain, system 10 (e.g., image-processing subsystem 120) may retrieve all sub-acquisition segments (e.g., L(1)-L(18)) that are associated with a given brain state, and reconstruct those sub-acquisition segments into a whole-brain fMRI image of only that given brain state.

In the illustrated embodiment, reconstructed whole-brain fMRI image 300 comprises a plurality of selectively combined groups of sub-acquisition segments L, associated with Brain State A. Specifically, system 10 (e.g., image-processing subsystem 120) may retrieve sub-acquisition segments group 230A (i.e., $L_1(1)$-$L_1(6)$ from fMRI image data 220), sub-acquisition segments group 230C (i.e., $L_2(7)$-$L_2(12)$ from fMRI image data 270), and sub-acquisition segments group 230B (i.e., $L_1(13)$-$L_1(18)$ from fMRI image data 220). As illustrated in FIGS. 2A and 2B, each group of sub-acquisition segments 230A, 230C, and 230B corresponds to Brain State A. Additionally, each individual sub-acquisition segment L(1) through L(18) in whole-brain fMRI image 300 corresponds to a different portion (e.g., line in k-space or slice in image-space) of the brain of the subject while Brain State A was active. Thus, system 10 (e.g., image-processing subsystem 120) combines these individual segments L(1) through L(18), selectively retrieved from a plurality of separately-acquired raw fMRI image data 220 and 270, into reconstructed whole-brain fMRI image 300. The reconstruction, from raw image data 220 and 270 to image 300, may be performed in k-space or image-space. If performed in k-space, the resulting image 300 may be subsequently converted to image-space (e.g., for graphical display) via Fourier transform.

In the illustrated embodiment, reconstructed whole-brain fMRI image 310 similarly comprises a plurality of selectively combined groups of sub-acquisition segments L, associated with Brain State B. Specifically, system 10 (e.g., image-processing subsystem 120) may retrieve sub-acquisition segments 280B (i.e., $L_2(1)$-$L_2(6)$ from fMRI image data 270), sub-acquisition segments 280A (i.e., $L_1(7)$-$L_1(12)$ from fMRI image data 220), and sub-acquisition segments 280C (i.e., $L_2(13)$-$L_2(18)$ from fMRI image data 270). As illustrated in FIGS. 2A and 2B, each group of sub-acquisition segments 280B, 280A, and 280C corresponds to Brain State B. Additionally, each individual sub-acquisition segment L(1) through L(18) in whole-brain fMRI image 310 corresponds to a different portion (e.g., line in k-space or slice in image-space) of the brain of the subject while Brain State B was active. Thus, system 10 (e.g., image-processing subsystem 120) combines these individual segments L(1) through L(18), selectively retrieved from a plurality of separately-acquired raw fMRI image data 220 and 270, into reconstructed whole-brain fMRI image 310. The reconstruction, from raw image data 220 and 270 to image 310, may be performed in k-space or image-space. If performed in k-space, the resulting image 310 may be subsequently converted to image-space (e.g., for graphical display) via Fourier transform.

Figure 3:
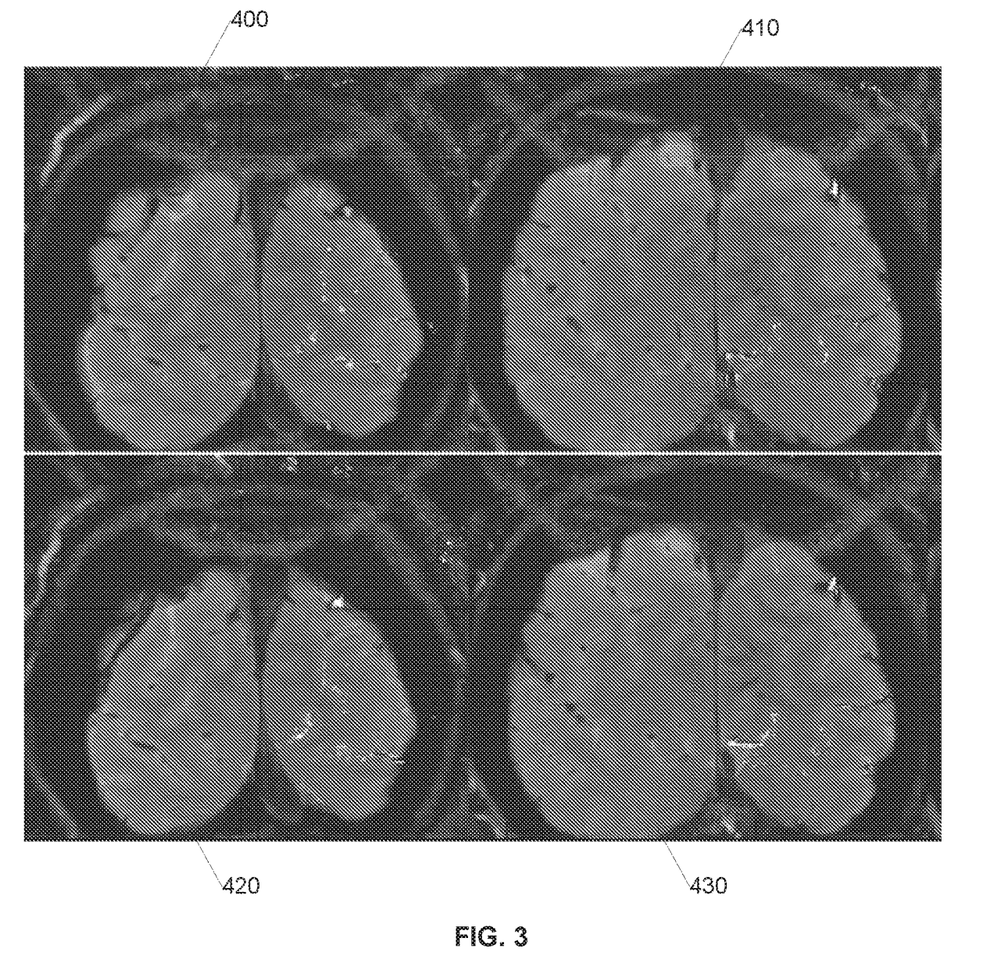
FIG. 3 is an fMRI image illustrating example coronal slices that were reconstructed according to an embodiment.

FIG. 3 is a whole-brain fMRI image illustrating example reconstructed coronal slices 400, 410, 420, and 430, according to an embodiment. In the illustrated embodiment, the coronal slices 400, 410, 420, and 430 were reconstructed from selectively combined fMRI image data in k-space. A thresholded activation map has been overlaid onto each coronal slice 400, 410, 420, and 430, based on the difference between "on" (e.g., Brain State A) and "off" (e.g., Brain State B) brain states. Brighter areas signify stronger activation, whereas darker areas signify weaker activation. The brain states were triggered in the subject's brain by a three-minute fMRI task, delivered to the subject by subject-stimulation subsystem 110. The fMRI task, in this case, was a block design, left-visual, hemi-field, flickering checkerboard that was "on" for eighteen seconds (e.g., corresponding to a first brain state) and then "off" for eighteen seconds (e.g., corresponding to a second brain state). The coronal slices were reconstructed in k-space from whole-brain fMRI image data that was acquired, across a plurality of acquisitions, while the stimulus (i.e., the fMRI task) was "on." The coronal slices were then converted from k-space to image-space, via Fourier transform, to produce the whole-brain fMRI image, illustrated in FIG. 3, comprising coronal slices 400, 410, 420, and 430.

Figure 4:
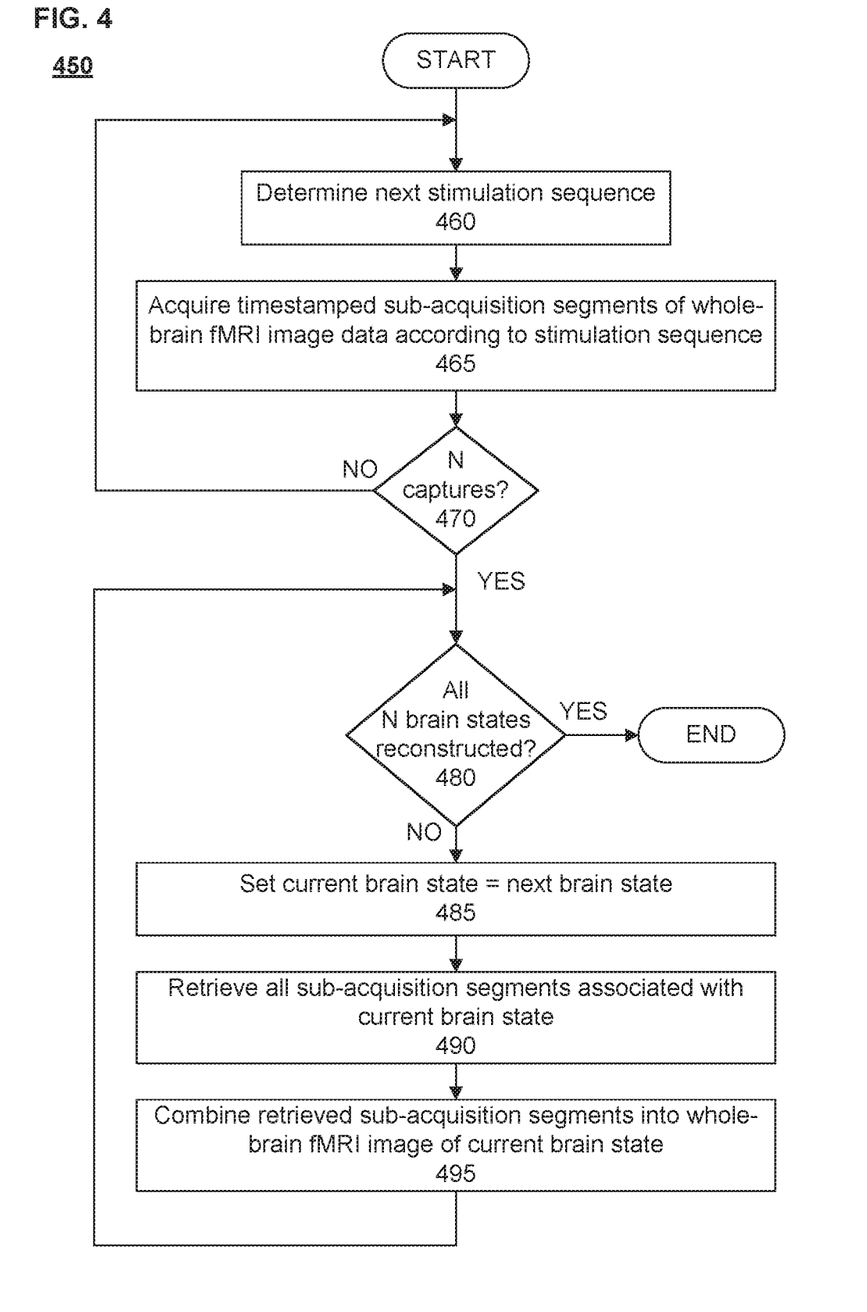
FIG. 4 is a flow diagram illustrating an example process for acquiring fMRI images, according to an embodiment.

FIG. 4 is a flow diagram illustrating an example process 450 for generating non-blurred (i.e., single-brain-state) whole-brain fMRI images, according to an embodiment. Process 450 may be implemented by system 10. For example, steps 460-470 may be performed by fMRI subsystem 100 in cooperation with subject-stimulation subsystem 110, and steps 480-495 may be performed by image-processing subsystem 120. While process 450 is illustrated with a certain arrangement of steps, process 450 may be implemented with fewer, more, or different steps and a different arrangement or ordering of steps.

Initially, the subject's head is positioned within an imaging chamber of fMRI subsystem 100. Then, a series of two or more loops (i.e., N loops, where N equals the number of brain states to be captured), defined by steps 460-470, are performed to acquire a plurality of raw whole-brain fMRI image data (e.g., fMRI image data 220 and 270) for the same region of the subject's brain (e.g., the same slice or the subject's entire brain, captured a plurality of times). As one of ordinary skill in the art would understand, this series of loops may be implemented in a myriad ways, as long as steps 460 and 465 are repeated N times with N different stimulation sequences, such that all sub-acquisition segments L are acquired once for each brain state.

In step 460, a stimulation sequence is determined for use in step 465. In an embodiment, the stimulation sequence is determined based on the number (i.e., N) of brain states to be captured, the length of time required to capture a whole-brain fMRI image (e.g., fMRI image data 220 or 270), and/or the length of time each brain state remains active upon stimulation. For example, the sequence determined in step 460 may be similar or identical to the sequence of A-B-A illustrated in FIG. 2A, in the event that two brain states are to be captured (i.e., N=2) and fMRI subsystem 100 requires a duration of three brain states (e.g., T1 to T4) to capture whole-brain fMRI image data for a particular region of the subject's brain. In this case, referring to FIG. 2A, the stimulation sequence may be defined as initiating stimulation from the beginning of fMRI capture at T1 to T2 of fMRI capture, terminating stimulation at T2 of fMRI capture, and reinitiating stimulation from T3 to T4 of fMRI capture. It should be understood that this is simply one illustrative, non-limiting example of a stimulation sequence, given example parameters.

In step 465, subject-stimulation system 110 stimulates the subject, according to the stimulation sequence determined in step 460. As discussed elsewhere herein, this stimulation may comprise a visual and/or aural stimulus, delivered by way of a visual display monitor and/or speaker of fMRI subsystem 100, and/or may comprise a user response or interaction received by way of a user input device of fMRI subsystem 100. Simultaneously with the performance of the stimulation sequence, fMRI subsystem 100 acquires raw fMRI image data of the subject's brain. As discussed elsewhere herein, this raw fMRI image data may be captured by fMRI subsystem 100, in k-space, as a plurality of sub-acquisition segments L (e.g., L(1)-L(18)). In this case, each sub-acquisition segment L may represent a line of k-space, such that, collectively, the sub-acquisitions segments L represent the entire k-space grid that the raw fMRI image data comprises.

As each sub-acquisition segment L is captured by fMRI subsystem 100 or sometime after each sub-acquisition segment L has been captured by fMRI subsystem 100, system 10 (e.g., fMRI subsystem 100 or subject-stimulation subsystem 110) associates the sub-acquisition segment with the coincident brain state of the subject, and may also associate the sub-acquisition segment with the brain region (e.g., slice) from which the sub-acquisition segment was acquired. For example, each sub-acquisition segment L may be time-stamped or otherwise annotated or labeled to temporally link the sub-acquisition segment with the presence or absence of a particular stimulus, which in turn links the sub-acquisition segment to the coincident brain state that results from the presence or absence of the particular stimulus. Additionally, in the case that the brain region being captured corresponds to a two-dimensional slice of the subject's brain, each sub-acquisition segment L may also be location-stamped to link the sub-acquisition segment with the particular brain slice to which the sub-acquisition segment corresponds. In this manner, if a plurality of two-dimensional slices are being captured (e.g., to generate a whole-brain three-dimensional fMRI image of the subject's brain), the sub-acquisition segments can be retrieved for a given brain slice (e.g., a current brain slice being processed) in a subsequent step (e.g., step 490).

In step 470, it is determined whether the whole-brain fMRI image data has been captured N times, i.e., using all N stimulation sequences necessary to capture each portion of the whole-brain fMRI image data in each of the N different brain states. If all N sets of whole-brain fMRI image data have been captured (i.e., "YES" in step 470), process 450 proceeds to step 480. Otherwise, if another set of whole-brain fMRI image data remains to be captured according to a new stimulation sequence (i.e., "NO" in step 470), process 450 returns to step 460.

After all N sets of whole-brain fMRI image data have been captured, a series of two or more logical loops (i.e., N loops), defined by steps 480-495, are performed to reconstruct the N sets of raw whole-brain fMRI image data (e.g., fMRI image data 220 and 270) into N whole-brain fMRI images (e.g., fMRI images 300 and 310). These loops may be performed serially or in parallel, depending on the capabilities of system 10 (e.g., image-processing subsystem 120). Again, as one of ordinary skill in the art would understand, this series of loops may be implemented in a myriad ways, as long as N whole-brain fMRI images are reconstructed in steps 490 and 495.

In step 480, it is determined whether all N brain states have been reconstructed. If all N brain states have been reconstructed (i.e., "YES" in step 480), process 450 ends. Otherwise, if another brain state remains to be reconstructed (i.e., "NO" in step 480), process 450 proceeds to step 485, in which the next brain state is set as the current brain state to be considered.

In step 490, each sub-acquisition segment, that is associated with the current brain state under consideration, is retrieved (e.g., from data storage area 15). For example, based on the stimulation sequences, determined through a plurality of iterations of step 460, image-processing subsystem 120 may identify timestamp ranges associated with each activation of the current brain state. Image-processing subsystem 120 may then retrieve all sub-acquisition segments that are associated with a timestamp within one of the identified timestamp ranges. This should result in the retrieval of a sub-acquisition segment representing each portion of the subject's brain captured in each iteration of step 465. For example, sub-acquisition segments for all of L(1)-L(18) should be retrieved in each iteration of step 490. Referring back to FIG. 2C, for Brain State A, groups 230A, 230C, and 230B would be retrieved in step 490. For Brain State B, groups, 280B, 280A, and 280C would be retrieved in step 490.

In step 495, the sub-acquisition segments (e.g., L(1)-L(18)), retrieved in step 490, are combined into a reconstructed whole-brain fMRI image of the current brain state according to their k-space and/or image-space location. For the example illustrated in FIGS. 2A and 2B, the sub-acquisition segments may be combined in the order in which they were acquired within their respective acquisitions. Referring back to FIG. 2C, since group 230A of sub-acquisition segments was captured first in the first acquisition, group 230C was captured second in the second acquisition, and group 230B was captured third in the first acquisition, they are ordered first, second, and third, respectively, in the reconstructed whole-brain fMRI image 300. Similarly, referring to FIG. 2D, since group 280B of sub-acquisition segments was captured first in the second acquisition, group 280A was captured second in the first acquisition, and group 280C was captured third in the second acquisition, they are ordered first, second, and third, respectively, in the reconstructed whole-brain fMRI image 310. After step 495, process 450 may return to step 480 to perform the reconstruction for any remaining brain states.

In the event that a plurality of two-dimensional slices of the brain are being captured, steps 490 and 495 may be performed for each two-dimensional slice of the brain being captured. In this case, in step 490, image-processing subsystem 120 may retrieve all sub-acquisition segments that are associated, not only with a timestamp within one of the timestamp ranges, associated with the current brain state, but that are also associated with the current region of the subject's brain (i.e., the current brain slice) under consideration. In other words, the sub-acquisition segments L(1)-L(18) may be retrieved based on both the brain state and the brain slice with which they are associated.

In addition, in the event that a plurality of two-dimensional slices of the brain are being captured, process 450 may be performed serially for each two-dimensional slice. Alternatively, steps 460-470 may be performed for each two-dimensional slice, prior to proceeding to step 480. In this case, as discussed above, steps 490 and 495 may be performed for each brain state and each two-dimensional slice.

As mentioned elsewhere herein, process 450 may be performed within k-space. In other words, in step 465, whole-brain fMRI image data is acquired in k-space, and, in step 495, the image data is reconstructed into images. In this case, each sub-acquisition segment may correspond to a line of the k-space of the whole-brain fMRI image data. At the end of process 450, the whole-brain fMRI images, constructed through multiple iterations of steps 490 and 495, may be converted to image-space via Fourier transform, to be displayed or otherwise used in different applications. Alternatively, process 450 may be performed entirely or partially within image-space, in which case each sub-acquisition segment may correspond to a region (e.g., a line of a two-dimensional brain slice, or a slice of a three-dimensional brain image) of the image-space.

In an embodiment, a computer-implemented method for acquiring whole-brain fMRI images, corresponding to a single brain state of a subject, comprises using an fMRI apparatus to acquire a plurality of whole-brain images of a brain of a subject, wherein each acquired whole-brain image comprises raw image data in k-space, and at least N of the plurality of whole-brain images comprise an N plurality of brain states (where N=2 in FIGS. 2A-2D). The method may additionally include identifying portions of the raw image data in k-space from the plurality of acquired whole-brain images that correspond to a first brain state and combining the identified portions of raw image data in k-space that correspond to the first brain state to generate raw image data in k-space for the whole brain of the subject that corresponds to the first brain state. The method may also include processing the raw image data in k-space for the whole brain of the subject that corresponds to the first brain state to generate a reconstructed first brain state image of the brain of the subject.

In an embodiment, the processing to generate a reconstructed first brain state image of the brain of the subject comprises performing a Fourier transform on the raw image data in k-space for the whole brain of the subject that corresponds to the first brain state. The method may further comprise stimulating the subject at a predetermined time to link the first brain state with one or more sub-acquisition segments of the raw image data in k-space. In one embodiment, a sub-acquisition segment comprises a single line of k-space. In an alternative embodiment, a sub-acquisition segment comprises an image slice.

The disclosed methods may be stored as executable programmed modules within a non-transitory computer-readable medium to be executed by a processor. Additionally or alternatively, the disclosed methods may be executed by at least one hardware processor that is comprised in a system, such as an fMRI apparatus.

3. Example Applications

The embodiments described herein generate whole-brain fMRI images, each representing a single brain state, and may be used in a variety of applications. For example, fMRI subsystem 100 may be used to acquire fMRI image data representing stimulus-related blood-oxygen-level dependent (BOLD) signals in the subject's brain. In this case, the resulting, reconstructed fMRI images can be used to analyze areas of brain activity during the various brain states.

However, the application of the disclosed embodiments is not limited to BOLD. For example, the same or similar embodiments may be applied to acquire images of four-dimensional (4D) flow velocity (e.g., to analyze stimulus-related blood-flow changes down to the arteriole and venule resolution), black blood (e.g., to analyze stimulus-related blood volume changes down to the arteriole and venule resolution), and/or the like. Given that the temporal resolution of the disclosed technique may be as fine as the duration of a single sub-acquisition segment (e.g., on the order of milliseconds), embodiments of the disclosed technique may be used to image highly dynamic systems and/or contrast mechanisms, such as neuronal currents, as long as their responses to input stimuli are reproducible and the signal-to-noise ratio is sufficient. In addition, the same or similar embodiments may be used with respiratory or cardiac navigation (e.g., to filter out artifacts due to respiration or cardiac-related pulsations), single-echo acquisition (e.g., simultaneous susceptibility-weighted venography with the fMRI acquisition for precise mapping of the vasculature to the detected BOLD activations), multi-echo acquisition (e.g., functional quantitative susceptibility imaging for enhanced contrast and both anatomical and biophysical characterization), compressed sensing (e.g., to accelerate the fMRI acquisition while maintaining data quality), prospective motion correction (e.g., using motion camera tracking in fMRI subsystem 100 to update the scanner gradients in real-time, to enable improved sharpness and reduced motion artifact in the resulting images), and/or the like.

4. Example Processing Device

Figure 5:
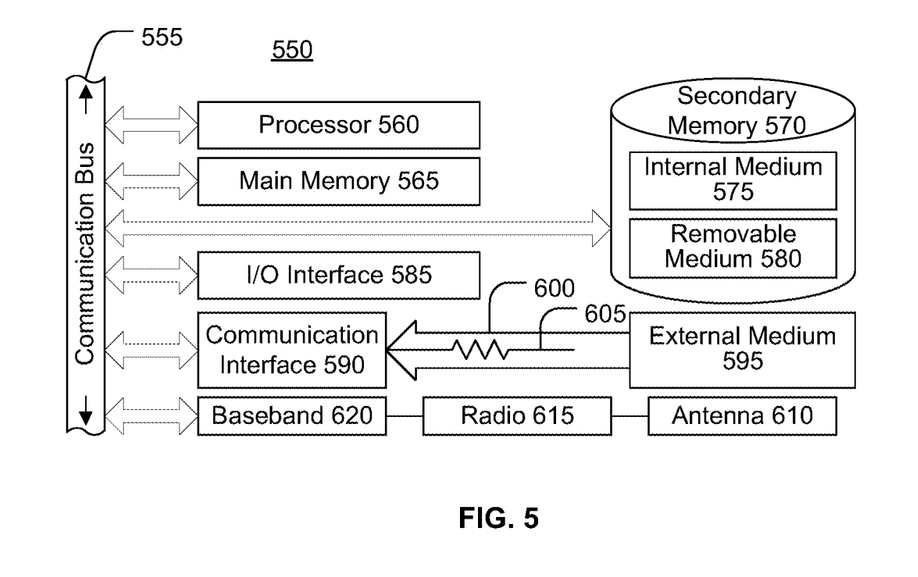
FIG. 5 is a block diagram illustrating an example processing device that may be used in connection with embodiments described herein.

FIG. 5 is a block diagram illustrating an example wired or wireless system 550 that may be used in connection with various embodiments described herein. For example the system 550 may be used as or in conjunction with system 10 and/or any of fMRI subsystem 100, subject-stimulation subsystem 110, and image-processing subsystem 120. The system 550 can be a conventional personal computer, computer server, personal digital assistant, smart phone, tablet computer, or any other processing device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating-point mathematical operations, a special-purpose microprocessor having an architecture suitable for fast execution of signal-processing algorithms (e.g., digital-signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560. Examples of processors which may be used with system 200 include, without limitation, the Pentium® processor, Core i7® processor, and Xeon® processor, all of which are available from Intel Corporation of Santa Clara, California.

Processor 560 is preferably connected to a communication bus 555. Communication bus 555 may include a data channel for facilitating information transfer between storage and other peripheral components of system 550. Furthermore, communication bus 555 may provide a set of signals used for communication with processor 560, including a data bus, address bus, and control bus (not shown). Communication bus 555 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, or standards promulgated by the Institute of Electrical and Electronics Engineers (IEEE) including IEEE 488 general-purpose interface bus (GPIB), IEEE 696/S-100, and the like.

System 550 preferably includes a main memory 565 and may also include a secondary memory 570. Main memory 565 provides storage of instructions and data for programs executing on processor 560, such as one or more of the processed described herein. It should be understood that programs stored in the memory and executed by processor 560 may be written and/or compiled according to any suitable language, including without limitation C/C++, Java, JavaScript, Perl, Visual Basic, .NET, and the like. Main memory 565 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

Secondary memory 570 may optionally include an internal memory 575 and/or a removable medium 580. Removable medium 580 is read from and/or written to in any well-known manner. Removable storage medium 580 may be, for example, a magnetic tape drive, a compact disc (CD) drive, a digital versatile disc (DVD) drive, other optical drive, a flash memory drive, and/or the like.

Secondary memory 570 is a non-transitory computer-readable medium having computer-executable code (e.g., disclosed software modules) and/or other data stored thereon. The computer software or data stored on secondary memory 570 is read into main memory 565 for execution by processor 560.

In alternative embodiments, secondary memory 570 may include other similar means for allowing computer programs or other data or instructions to be loaded into system 550. Such means may include, for example, a communication interface 590, which allows software and data to be transferred from external storage medium 595 to system 550. Examples of external storage medium 595 may include an external hard disk drive, an external optical drive, an external magneto-optical drive, and/or the like. Other examples of secondary memory 570 may include semiconductor-based memory such as programmable read-only memory (PROM), erasable programmable read-only memory (EPROM), electrically erasable read-only memory (EEPROM), or flash memory (block-oriented memory similar to EEPROM).

As mentioned above, system 550 may include a communication interface 590. Communication interface 590 allows software and data to be transferred between system 550 and external devices (e.g. printers), networks, or other information sources. For example, computer software or executable code may be transferred to system 550 from a network server (e.g., platform 110) via communication interface 590. Examples of communication interface 590 include a built-in network adapter, network interface card (NIC), Personal Computer Memory Card International Association (PCMCIA) network card, card bus network adapter, wireless network adapter, Universal Serial Bus (USB) network adapter, modem, a network interface card (NIC), a wireless data card, a communications port, an infrared interface, an IEEE 1394 fire-wire, or any other device capable of interfacing system 550 with a network or another computing device. Communication interface 590 preferably implements industry-promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 590 are generally in the form of electrical communication signals 605. These signals 605 may be provided to communication interface 590 via a communication channel 600. In an embodiment, communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer-executable code (e.g., implementing the disclosed processes) is stored in main memory 565 and/or secondary memory 570. Computer programs can also be received via communication interface 590 and stored in main memory 565 and/or secondary memory 570. Such computer programs, when executed, enable system 550 to perform the various processes of the disclosed embodiments as described elsewhere herein.

In this description, the term "computer-readable medium" is used to refer to any non-transitory computer-readable storage media used to provide computer-executable code to or within system 550. Examples of such media include main memory 565, secondary memory 570 (including internal memory 575, removable medium 580, and external storage medium 595), and any peripheral device communicatively coupled with communication interface 590 (including a network information server or other network device). These non-transitory computer-readable mediums are means for providing executable code, programming instructions, and software to system 550.

In an embodiment that is implemented using software, the software may be stored on a computer-readable medium and loaded into system 550 by way of removable medium 580, I/O interface 585, or communication interface 590. In such an embodiment, the software is loaded into system 550 in the form of electrical communication signals 605. The software, when executed by processor 560, preferably causes processor 560 to perform one or more of the processes and functions described elsewhere herein.

In an embodiment, I/O interface 585 provides an interface between one or more components of system 550 and one or more input and/or output devices. Example input devices include, without limitation, sensors, keyboards, touch screens or other touch-sensitive devices, biometric sensing devices, computer mice, trackballs, pen-based pointing devices, and/or the like. Examples of output devices include, without limitation, other processing devices, cathode ray tubes (CRTs), plasma displays, light-emitting diode (LED) displays, liquid crystal displays (LCDs), printers, vacuum fluorescent displays (VFDs), surface-conduction electron-emitter displays (SEDs), field emission displays (FEDs), and the like.

System 550 may also include optional wireless communication components that facilitate wireless communication over a voice network and/or a data network. The wireless communication components comprise an antenna system 610, a radio system 615, and a baseband system 620. In system 550, radio frequency (RF) signals are transmitted and received over the air by antenna system 610 under the management of radio system 615.

In one embodiment, antenna system 610 may comprise one or more antennae and one or more multiplexors (not shown) that perform a switching function to provide antenna system 610 with transmit and receive signal paths. In the receive path, received RF signals can be coupled from a multiplexor to a low noise amplifier (not shown) that amplifies the received RF signal and sends the amplified signal to radio system 615.

In an alternative embodiment, radio system 615 may comprise one or more radios that are configured to communicate over various frequencies. In an embodiment, radio system 615 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from radio system 615 to baseband system 620.

If the received signal contains audio information, then baseband system 620 decodes the signal and converts it to an analog signal. Then the signal is amplified and sent to a speaker. Baseband system 620 also receives analog audio signals from a microphone. These analog audio signals are converted to digital signals and encoded by baseband system 620. Baseband system 620 also codes the digital signals for transmission and generates a baseband transmit audio signal that is routed to the modulator portion of radio system 615. The modulator mixes the baseband transmit audio signal with an RF carrier signal generating an RF transmit signal that is routed to antenna system 610 and may pass through a power amplifier (not shown). The power amplifier amplifies the RF transmit signal and routes it to antenna system 610, where the signal is switched to the antenna port for transmission.

Baseband system 620 is also communicatively coupled with processor 560, which may be a central processing unit (CPU). Processor 560 has access to data storage areas 565 and 570. Processor 560 is preferably configured to execute instructions (i.e., computer programs, such as the disclosed application, or software modules) that can be stored in main memory 565 or secondary memory 570. Computer programs can also be received from baseband processor 620 and stored in main memory 565 or in secondary memory 570, or executed upon receipt. Such computer programs, when executed, enable system 550 to perform the various processes of the disclosed embodiments.

The above description of the disclosed embodiments is provided to enable any person skilled in the art to make or use the invention. Various modifications to these embodiments will be readily apparent to those skilled in the art, and the general principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

The invention claimed is:

1. A method comprising using at least one hardware processor to:
for each sensory stimulation sequence of a plurality of sensory stimulation sequences applied to a subject, control a functional Magnetic Resonance Imaging (fMRI) apparatus to capture a corresponding set of whole-brain image data of a plurality of corresponding sets of whole-brain image data of a same region of a brain of the subject, wherein a first temporal order of sensory stimulations of a first sensory stimulation sequence of the plurality of sensory stimulation sequences applied to the subject is configured to induce a first induction sequence of a first group of brain states of a plurality of brain states and a second temporal order of sensory stimulations of a second sensory stimulation sequence of the plurality of sensory stimulation sequences applied to the subject is configured to induce a second induction sequence of a second group of brain states of the plurality of brain states, wherein a first order of induction of the brain states in the first induction sequence of the first group of brain states of the plurality of brain states is different than a second order of induction of the brain states in the second induction sequence of the second group of brain states of the plurality of brain states, and wherein each corresponding captured set of the whole-brain image data of the plurality of corresponding captured sets of whole-brain image data comprises a plurality of sub-acquisition segments;
for each corresponding captured set of the whole-brain image data of the plurality of corresponding captured sets of whole-brain image data, temporally associate each sub-acquisition segment of the plurality of sub-acquisition segments in the corresponding captured set of whole-brain image data with at least one brain state of the plurality of brain states included in the second and first groups of brain states; and
for the at least one brain state of the plurality of brain states, reconstruct a corresponding whole-brain image from a subset of the plurality of sub-acquisition segments in each corresponding captured set of the whole-brain image data of the plurality of corresponding captured sets of whole-brain image data that are temporally associated with the at least one brain state of the plurality of brain states included in the second and first groups of brain states.

2. The method of claim 1, wherein temporally associating each sub-acquisition segment of the plurality of sub-acquisition segments in the corresponding set of whole-brain image data with the at least one brain state of the plurality of brain states comprises, for each sub-acquisition segment of the plurality of sub-acquisition segments in the corresponding set of whole-brain image data:
after each sub-acquisition segment of the plurality of sub-acquisition segments is captured, storing each corresponding sub-acquisition segment of the plurality of sub-acquisition segments in temporal association with a corresponding timestamp indicating a time at which each corresponding sub-acquisition segment of the plurality of sub-acquisition segments was captured; and
determining an activated brain state of the plurality of brain states that was active at the time at which each sub-acquisition segment of the plurality of sub-acquisition segments was captured, based on the first or second stimulation sequence of the plurality of sensory stimulation sequences applied to the subject at the time each corresponding sub-acquisition segments of the plurality of sub-acquisition segments was captured during the capture the corresponding set of whole-brain image data of the plurality of corresponding sets of while-brain image data.

3. The method of claim 1, further comprising determining the plurality of sensory stimulation sequences, such that:
each of the first sensory stimulation sequence of the plurality of sensory stimulation sequences and the second sensory stimulation sequence of the plurality of sensory stimulation sequences comprise a plurality of time periods;
in a first time period of the plurality of time periods, a first brain state of the plurality of brain states is induced by the first sensory stimulation sequence and a second brain state of the plurality of brain states is induced by the second sensory stimulation sequence, wherein the at least one brain state is either the first or second brain state;
in a second time period of the plurality of time periods, the second brain state of the plurality of brain states is induced by the first sensory stimulation sequence and the first brain state of the plurality of brain states is induced by the second sensory stimulation sequence; and
across all of the plurality of sensory stimulation sequences, all of the plurality of brain states are induced at least once in each of the plurality of time periods.

4. The method of claim 1, wherein a total quantity of the sensory stimulation sequences of the plurality of sensory stimulation sequences is greater than or equal in quantity to the total quantity of the plurality of brain states.

5. The method of claim 1, wherein each set of whole-brain image data of the plurality of corresponding sets of whole-brain image data and the reconstructed whole-brain image has a spatial resolution of 0.03 mm$^3$ or greater.

6. The method of claim 1, wherein the same region of the brain is a two-dimensional slice of the brain, such that each corresponding captured set of the whole-brain image data of the plurality of corresponding captured sets of whole-brain image data and the corresponding reconstructed whole-brain image represents a two-dimensional cross-section of the brain.

7. The method of claim 6, further comprising:
performing:
the control of the fMRI apparatus to capture the corresponding captured set of the whole-brain image data of the plurality of corresponding sets of while-brain image data of the same regions of the brain of the subject,
the temporal association of each sub-acquisition segment of the plurality of sub-acquisition segments in the corresponding captured set of whole-brain image data with at least one of the plurality of brain states included in the second and first groups of brain states, and
the reconstruction of the two-dimensional slice of the brain; and
for the at least one brain state of the plurality of brain states, combining the corresponding reconstructed whole-brain image with additional corresponding reconstructed whole brain images temporally associated with the at least one brain state into an updated set of reconstructed whole-brain images representing the brain in three dimensions.

8. The method of claim 1, wherein the first and second groups of brain states of the plurality of brain states comprise a first brain state and a second brain state, and wherein each of the first and second sensory stimulation sequences of the plurality of sensory stimulation sequences comprises at least one sensory stimulation being applied to the subject for induction of the first brain state.

9. The method of claim 8, wherein the second brain state is induced by absence of the at least one sensory stimulation being applied to the subject for induction of the first brain state.

10. The method of claim 1, wherein each corresponding captured set of the whole-brain image data of the plurality of corresponding captured sets of whole-brain image data is captured in k-space, and wherein the corresponding reconstructed whole-brain image is reconstructed in k-space.

11. The method of claim 10, wherein each sub-acquisition segment in the subset of the plurality of sub-acquisition segments consists of a line of k-space.

12. The method of claim 10, further comprising-converting the corresponding reconstructed whole-brain image from k-space to image-space using a Fourier transform.

13. The method of claim 1, wherein controlling the fMRI apparatus to capture the corresponding set of whole-brain image data of the plurality of corresponding sets of whole-brain image data of the same region of the brain of the subject comprises, while the fMRI apparatus is imaging the same region of the brain, providing one or more sensory stimuli to the subject at one or more times specified in the first or second sensory stimulation sequence of the plurality of sensory stimulation sequences.

14. The method of claim 13, wherein the one or more stimuli comprise a visual stimulus and/or an auditory stimulus.

15. The method of either claim 13, wherein the one or more stimuli comprise a tactile stimulus and/or an olfactory stimulus.

16. A system comprising:
at least one hardware processor; and
one or more software modules that, when executed by the at least one hardware processor,
for each sensory stimulation sequence of a plurality of sensory stimulation sequences applied to a subject, control a functional Magnetic Resonance Imaging (fMRI) apparatus to capture a corresponding set of whole-brain image data of a plurality of corresponding sets of whole-brain image data of a same region of a brain of the subject, wherein a first temporal order of sensory stimulations of a first sensory stimulation sequence of the plurality of sensory stimulation sequences applied to the subject is configured to induce a first induction sequence of a first group of brain states of a plurality of brain states and a second temporal order of sensory stimulations of a second sensory stimulation sequence of the plurality of sensory stimulation sequences applied to the subject is configured to induce a second induction sequence of a second group of brain states of the plurality of brain states, wherein a first order of induction of the brain states in the first induction sequence of the first group of brain states of the plurality of brain states is different than a second order of induction of the brain states in the second induction sequence of the second group of brain states of the plurality of brain states, and wherein each corresponding captured set of the whole-brain image data of the plurality of corresponding captured sets of whole-brain image data comprises a plurality of sub-acquisition segments;
for each corresponding captured set of the whole-brain image data of the plurality of corresponding captured sets of whole-brain image data, temporally associate each sub-acquisition segment of the plurality of sub-acquisition segments in the corresponding captured set of whole-brain image data with at least one brain state of the plurality of brain states included in the second and first groups of brain states; and
for the at least one brain state of the plurality of brain states, reconstruct a corresponding whole-brain image from a subset of the plurality of sub-acquisition segments in each corresponding captured set of the whole-brain image data of the plurality of corresponding captured sets of whole-brain image data that are temporally associated with the at least one brain state of the plurality of brain states included in the second and first groups of brain states.

17. The system of claim 16, wherein each corresponding captured set of the whole-brain image data of the plurality of corresponding captured sets of whole-brain image data is captured in k-space, and wherein the corresponding reconstructed whole-brain image is reconstructed in k-space.

18. The system of claim 16, wherein each sub-acquisition segment in the subset of the plurality of sub-acquisition segments consists of a line of k-space.

19. The system of claim 16, wherein the same region of the brain is a two-dimensional slice of the brain, such that each corresponding captured set of the whole-brain image data of the plurality of corresponding captured sets of whole-brain image data and the corresponding reconstructed whole-brain image represents a two-dimensional cross-section of the brain.

20. A non-transitory computer-readable medium having instructions stored thereon, wherein the instructions, when executed by a processor, cause the processor to:
for each sensory stimulation sequence of a plurality of sensory stimulation sequences applied to a subject, control a functional Magnetic Resonance Imaging (fMRI) apparatus to capture a corresponding set of whole-brain image data of a plurality of corresponding sets of whole-brain image data of a same region of a brain of the subject, wherein a first temporal order of sensory stimulations of a first sensory stimulation sequence of the plurality of sensory stimulation sequences applied to the subject is configured to induce a first induction sequence of a first group of brain states of a plurality of brain states and a second temporal order of sensory stimulations of a second sensory stimulation sequence of the plurality of sensory stimulation sequences applied to the subject is configured to induce a second induction sequence of a second group of brain states of the plurality of brain states, wherein a first order of induction of the brain states in the first induction sequence of the first group of brain states of the plurality of brain states is different than a second order of induction of the brain states in the second induction sequence of the second group of brain states of the plurality of brain states, and wherein each corresponding captured set of the whole-brain image data of the plurality of corresponding captured sets of whole-brain image data comprises a plurality of sub-acquisition segments;

for each corresponding captured set of the whole-brain image data of the plurality of corresponding captured sets of whole-brain image data, temporally associate each sub-acquisition segment of the plurality of sub-acquisition segments in the corresponding captured set of whole-brain image data with at least one brain state of the plurality of brain states included in the second and first groups of brain states; and for the at least one brain state of the plurality of brain states, reconstruct a corresponding whole-brain image from a subset of the plurality of sub-acquisition segments in each corresponding captured set of the whole-brain image data of the plurality of corresponding captured sets of whole-brain image data that are temporally associated with the at least one brain state of the plurality of brain states included in the second and first groups of brain states.

* * * * *